United States Patent [19]
Yoshimoto et al.

[11] Patent Number: 5,322,263
[45] Date of Patent: Jun. 21, 1994

[54] ENDOSCOPE SUCTION OPERATING APPARATUS

[75] Inventors: Yosuke Yoshimoto; Yasuyuki Futatsugi; Yoshio Tashiro, all of Hachioji, Japan

[73] Assignee: Olympus Optical Co., Ltd., Tokyo, Japan

[21] Appl. No.: 105,129

[22] Filed: Aug. 12, 1993

Related U.S. Application Data

[62] Division of Ser. No. 824,773, Jan. 23, 1992, Pat. No. 5,257,773.

[30] Foreign Application Priority Data

Jan. 25, 1991 [JP] Japan .................. 3-025551
Oct. 9, 1991 [JP] Japan .................. 3-262438
Dec. 19, 1991 [JP] Japan .................. 3-337134

[51] Int. Cl.⁵ .................. F16K 31/00; F16K 31/44
[52] U.S. Cl. .................. 251/251; 128/4; 251/263; 251/339; 251/342
[58] Field of Search ............ 251/251, 263, 319, 320, 251/321, 322, 323, 339, 342, 347, 354; 128/4, 4 A

[56] References Cited

U.S. PATENT DOCUMENTS

| | | | |
|---|---|---|---|
| 877,875 | 1/1908 | Van Nostran | 251/278 |
| 935,842 | 10/1909 | Foley | 251/278 |
| 3,958,566 | 5/1976 | Furihata | 128/4 A |
| 4,469,090 | 9/1984 | Konomura | 128/4 A |
| 4,537,209 | 8/1985 | Sasa | 128/4 A |
| 4,561,428 | 12/1985 | Konomura | 128/4 A |
| 4,562,830 | 1/1986 | Yabe | 128/4 A |
| 4,915,348 | 4/1990 | Speidel | 251/278 |

*Primary Examiner*—George L. Walton
*Attorney, Agent, or Firm*—Armstrong, Westerman, Hattori, McLeland & Naughton

[57] ABSTRACT

A suction operating apparatus in an endoscope consisting of an outer cylinder connected to a sucking channel of the endoscope, an inner cylinder removably fitted to this outer cylinder and having a sucking hole on the side, a valve body made of an elastic material and having a slit in a closing part provided in the lower end part of this inner cylinder and closing a lower end opening of the inner cylinder, an operating member provided so as to be free to advance and retreat within the inner cylinder, and to be pushed into the slit of the valve body to open and close this slit, thus forming a fluid flow path communicating with the sucking hole in the axial direction, and an elastic cover for elastically returning the operating member to the fixed position from the pushed-in position.

11 Claims, 19 Drawing Sheets

ENDOSCOPE SUCTION OPERATING APPARATUS

This is a division of application Ser. No. 07/824,773, filed Jan. 23, 1992.

BACKGROUND OF THE INVENTION

1. Field of the Invention

This invention relates to an endoscope suction operating apparatus to be used to suck dirt and body fluids within a body cavity.

2. Description of the Related Art

Generally, a suction operating apparatus is provided in the operating part of an endoscope so that dirt and body fluids within a body cavity may be sucked out of the body cavity through a sucking channel by operating this suction operating apparatus. So far, in this kind of suction operating apparatus, as shown, for example, in the publication of Japanese utility model application laid open No. 80102/1989, such suction has been made by opening with an operating member a valve body provided between a sucking port and sucking channel within a cylinder connected to the sucking channel and closing with an elastic member a leaking clearance making the sucking port communicate with the atmosphere through a cylinder.

However, in such suction operating apparatus, a small diameter part acting as a valve seat is provided within the cylinder, a piston valve is pressed against this small diameter part and is separated from the small diameter part to suck the sucking channel. The inside surface of the cylinder is of a complicated form and is hard to wash. In the prior art the back side of the small diameter part is not well washed and is prone to being a contagious source of germs.

The valve body particularly having a slit is prone to retain dirt and it is desirable that it be easy to remove, wash or replace.

Therefore, suction operating apparatus is desired wherein the operating member and the like can be easily removed to be washed and the cylinder interior is of a form easy to wash.

SUMMARY OF THE INVENTION

An object of the present invention is to provide an endoscope suction operating apparatus wherein the cylinder interior can be made in a simple form easy to wash and the contagion caused by bad washing can be prevented.

Another object of the present invention is to provide an endoscope suction operating apparatus wherein the operating member which opens and closes the valve body provided within the cylinder can be easily fitted, removed and disassembled and the respective component members can be positively washed.

Another object of the present invention is to provide an endoscope suction operating apparatus wherein, while securing a sufficient leaking flow volume at the time of non-suction and yet at the time of suction, no sucked substance will spread out to be deposited on the operator or the like and a safe and positive suction can be made.

The suction operating apparatus according to the present invention comprises an outer cylinder connected to a sucking channel of an endoscope, an inner cylinder removably fitted to this outer cylinder and having a sucking hole on the side, a valve body made of an elastic material and having a slit in a closing part thereof and being attached to a lower end open part of this inner cylinder for closing a lower end opening of the above-mentioned inner cylinder, wherein the lower end open part is defined by the slit an operating member provided so as to be free to advance and retreat within the above-mentioned inner cylinder, thereby pushing into the slit of the above-mentioned valve body to open and close the slit and forming a fluid flow path through the operating member communicating with the above-mentioned sucking hole in the axial direction and an elastic returning means attached to an upper end of the operating member and at least one of the inner cylinder and an upper end of the outer cylinder, wherein the elastic returning means is capable of elastically returning the above-mentioned operating member to the fixed position from the pushed-in position.

The other features and advantages of the present invention will become apparent enough with the following explanation.

BRIEF DESCRIPTION OF THE DRAWINGS

FIGS. 1 to 9 relate to the first embodiment of the present invention.

FIG. 1 is a perspective view showing a schematic formation of an endoscope.

FIG. 2 is a sectioned view showing the formation of a suction operating apparatus in the first embodiment.

FIG. 3 is a sectioned view on line A—A in FIG. 2.

FIG. 4 is an elevation of a suction operating apparatus.

FIG. 5 is a sectioned view showing the interior of a gripping part.

FIG. 6 is an explanatory view for explaining the operation of the first embodiment.

FIG. 7 is a sectioned view on line C—C in FIG. 6.

FIG. 9 is a view showing a modification of an outer cylinder.

FIG. 10 is a perspective view showing a schematic formation of an endoscope.

FIG. 11 is a sectioned view showing the formation of a suction operating apparatus in the second embodiment.

FIG. 12 is an elevation of a suction operating valve.

FIG. 13 is a view showing the lower surface of the same suction operating valve.

FIG. 14 is a sectioned view showing the interior of the operating part.

FIGS. 15 and 16 relate to the third embodiment of the present invention.

FIG. 15 (a) is a sectioned view of a suction operating apparatus.

FIG. 18 is a sectioned view showing a suction operating apparatus of the fifth embodiment as no sucking operation is being made.

FIG. 19 is a sectioned view showing the suction operating apparatus as a sucking operation is being made.

FIG. 20 is a sectioned view showing the suction operating apparatus as the sucking operation has been made.

FIG. 21 is a sectioned view showing a non-sucking state and sucking state as magnified.

FIG. 22 is a sectioned view showing the use with no cover fitted.

FIG. 23 is an explanatory view showing a valve body being removed by using a cover.

DETAILED DESCRIPTION OF THE PREFERRED EMBODIMENTS

FIGS. 1 to 9 show the first embodiment of the present invention.

Figure 1:
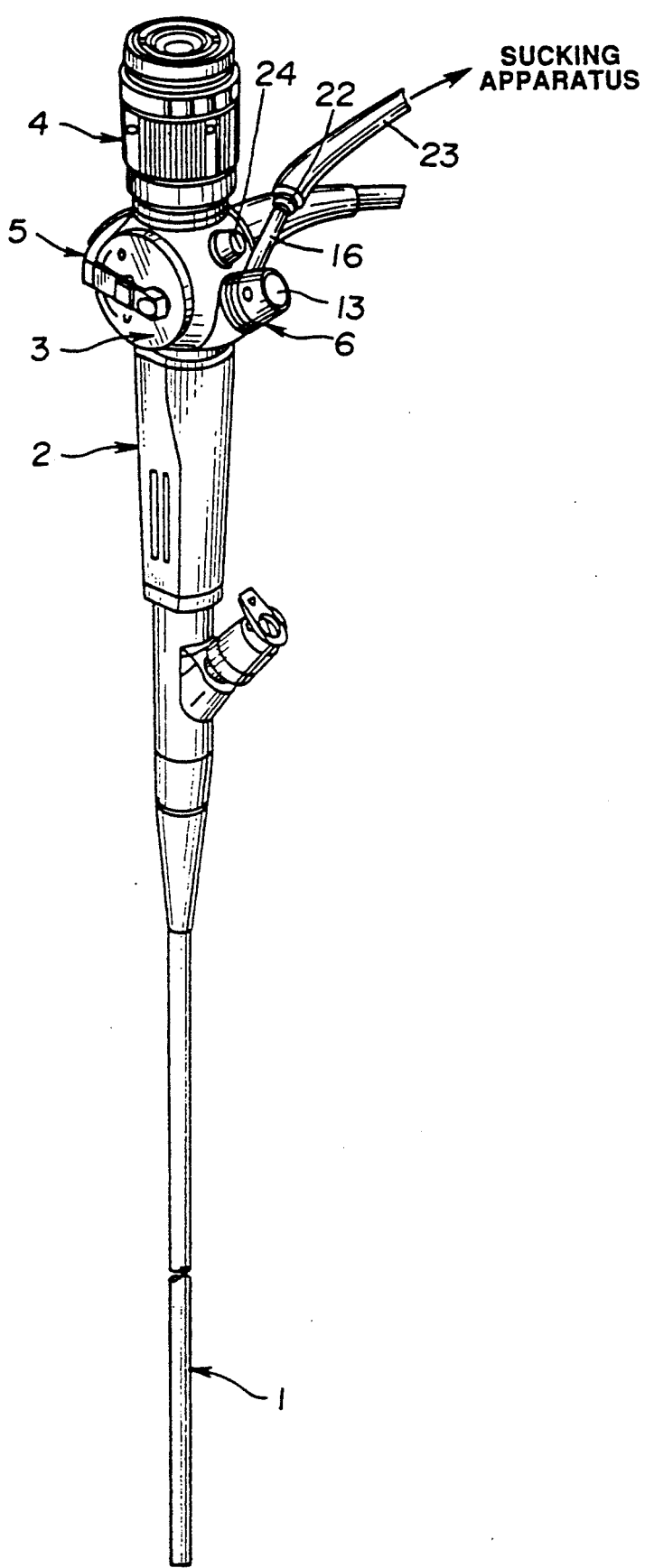

FIG. 1 is a view showing a schematic formation of an endoscope provided with a suction operating apparatus of this embodiment. This endoscope is provided with a gripping part at the rear end of an insertable part 1 to be inserted into a body cavity. The endoscope is further provided with an operating part 3 and eyepiece part 4 at the rear end of the gripping part 2, a bending operation lever 5 for bending the tip part of the insertable part in the operating part 3 and a suction operating apparatus 6 for suction from a treating instrument channel formed within the insertable part 1 through a sucking channel communicating with this treating instrument channel.

In the sucking operation apparatus 6 fitted to this operating part 3, a pipe-like mouthpiece part 16 is extended out of the side outside the operating part 3 and a sucking tube 23 connected to such sucking apparatus as a sucking pump, not illustrated, is fitted to a connecting part 22 at the end of this mouthpiece part 16. In this suction operating apparatus 6, a suction operating part 13 for operating suction is formed at the top so that the suction may be operated by pushing in the suction operating part 13 with the finger holding the operating part 3.

Figure 2:
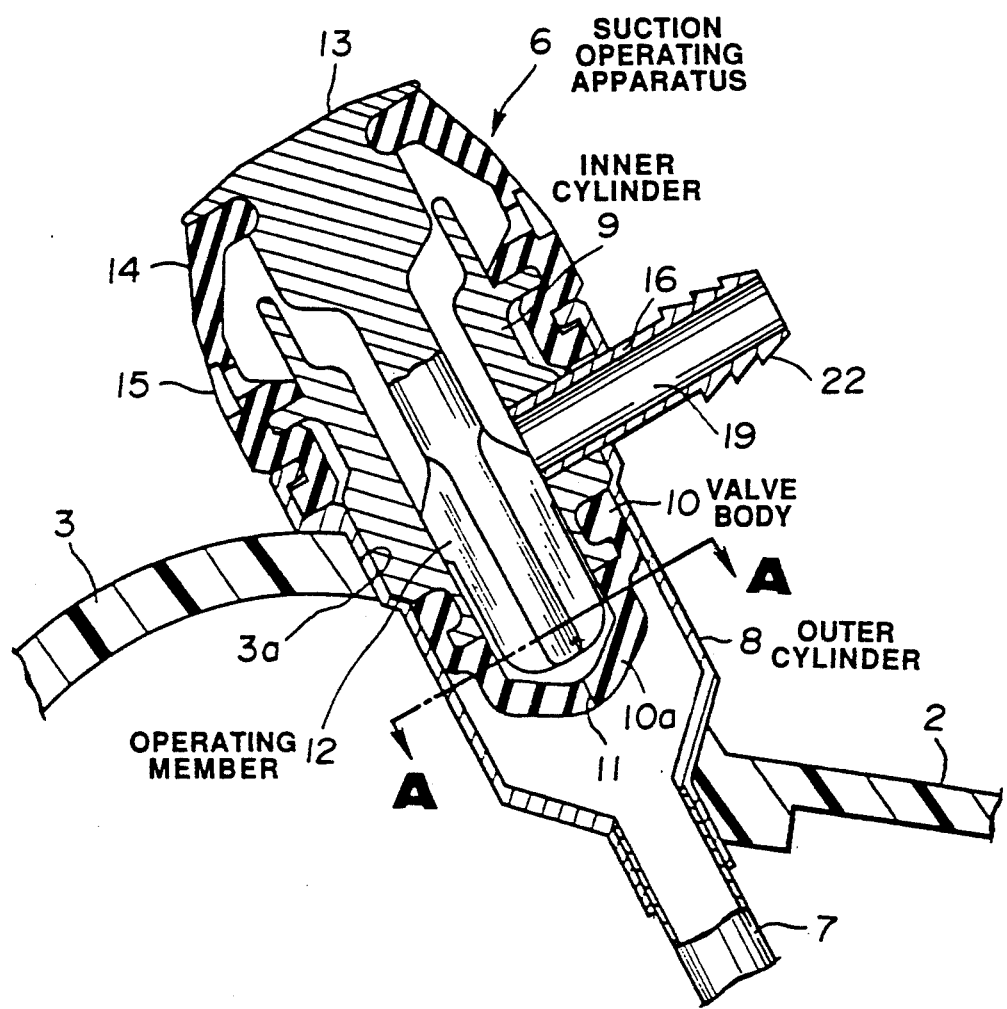

The formation of the above-mentioned suction operating apparatus 6 is shown in FIG. 2. In FIG. 2, the reference numeral 7 represents a sucking channel communicating with a treating instrument channel, not illustrated, an outer cylinder 8 of the suction operating apparatus 6 which is an embodiment of the present invention is connected to this sucking channel 7. An inner cylinder 9 is removably fitted to this outer cylinder 8 and is provided at the lower end with a valve body 10 made of an elastic material, such as rubber. This valve body 10 is substantially cylindrical and is provided in the lower part with a dome-like closing film 10a closing an opening at the lower end of the inner cylinder 9. A slit 11 is formed in the central part of the closing film 10a. A sucking plug body is formed of the outer cylinder 8 and inner cylinder 9.

Figure 3:
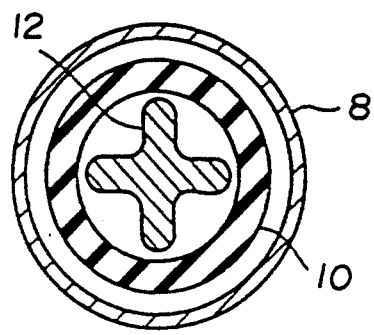

Also, a bar-like operating member 12 is provided within the inner cylinder so as to be free to advance and retreat by a predetermined stroke in the axial direction, is cruciform in the cross-section as shown in FIG. 3 and is provided at the upper end with an operating part 13 to push the closing film 10a of the valve body 10 with the lower end so as to be able to open the slit 11.

The inner cylinder 9 is provided at the upper end with a cover 14 as an elastic cylindrical member forming an elastic returning means so as to cover the periphery of the operating member 12. This cover 14 is made of an elastic material, such as rubber, is shaped to be cylindrically tapered in the upper part and is elastic in the axial direction of the cylinder. The operating member 12 is energized so as to return to the predetermined position by the elastic force of the cover 14 after it is pushed down. The cover 14 has a leaking hole 15 formed so that, when the operating member 12 is not operated, the interior of the inner cylinder 9 will communicate with and suck the atmosphere.

Figure 4:
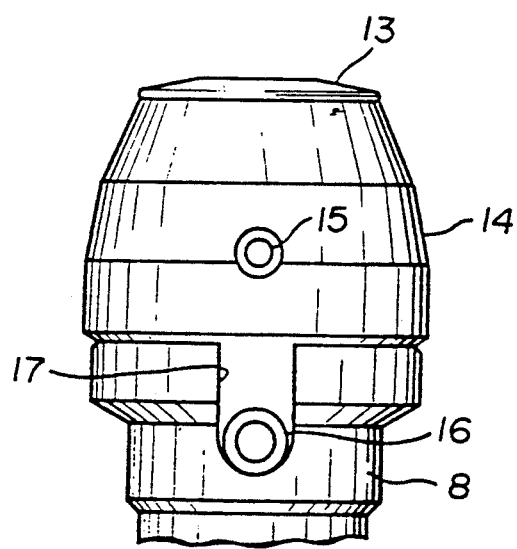

Also, the inner cylinder 9 is provided on the side with a mouthpiece part 16 forming a sucking path 19. The connecting part 22 at the tip of this mouthpiece part 16 is so made that a sucking pump, not illustrated, may be connected through a sucking tube and the dirt and body fluids within the body cavity may be sucked by the sucking force of the sucking pump. As shown in FIG. 4, the base end part of the mouthpiece part 16 is engaged with an incised part 17 formed in the cylinder 8.

As shown in FIG. 1, the above-mentioned mouthpiece part 16 is pulled out in a direction out of the way of operating, for example, the switch 24 provided as another operating means in the operating part 3. For example, in case this suction operating apparatus 6 is to be fitted to the hole 3a (see FIG. 2) formed in the operating part 3, the pipe-like mouthpiece part 16 will be positioned in the peripheral direction so as to be pulled out somewhat toward the eyepiece part 4 from the just side of the outer cylinder 8 to be the cylindrical part of the suction operating apparatus part 6. The suction and switch can thus be easily operated.

Figure 5:
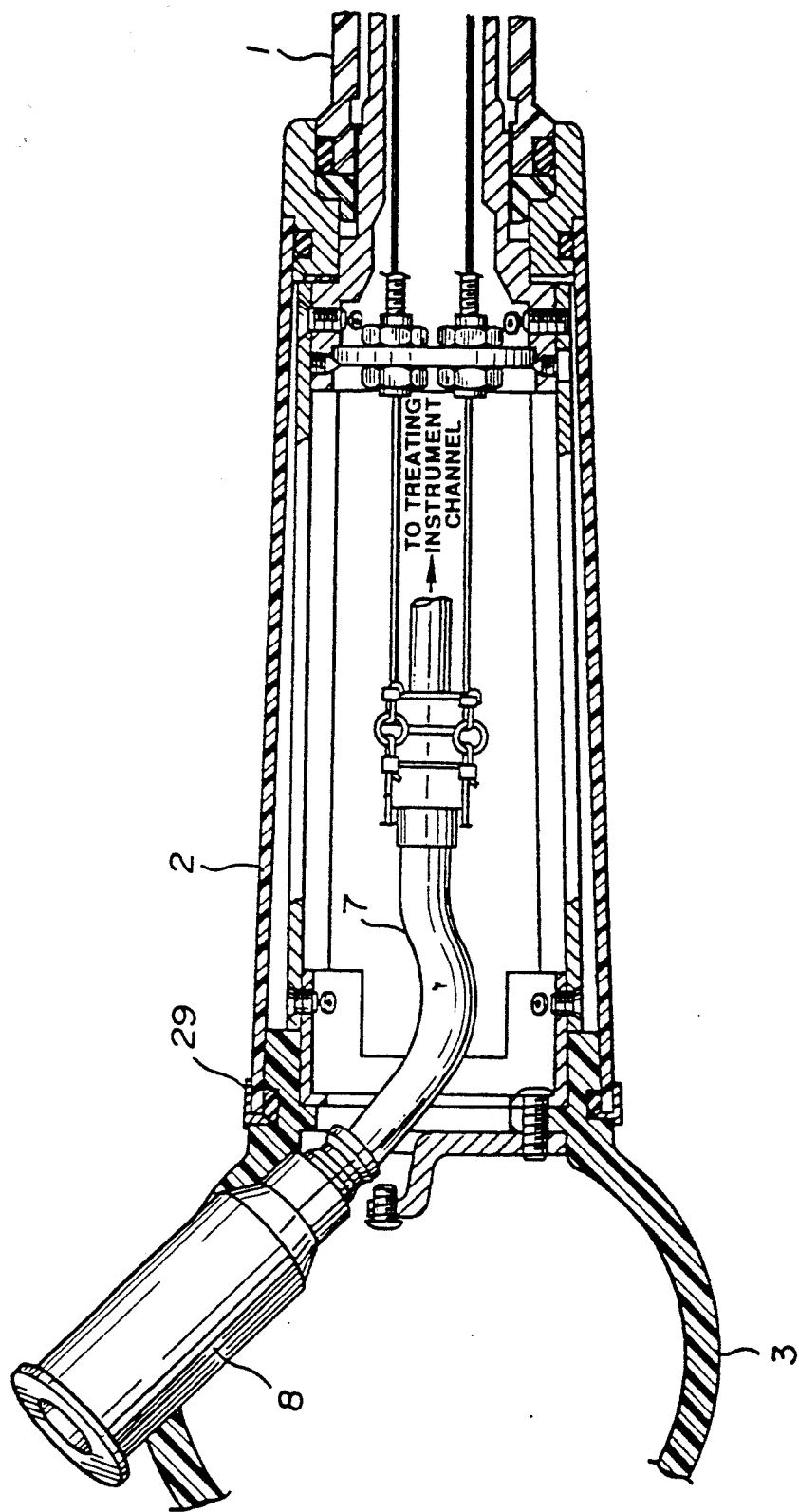

FIG. 5 is a sectioned view showing the interior of the gripping part 2. As shown in FIG. 5, the sucking channel 7 connected to the outer cylinder 8 is inserted through the gripping part 2 and communicates with a treating instrument channel, not illustrated, formed within the insertable part 1. A ring-like pressing member 29 is provided in the connecting part of the gripping part 2 and operating part 3.

Figure 6:
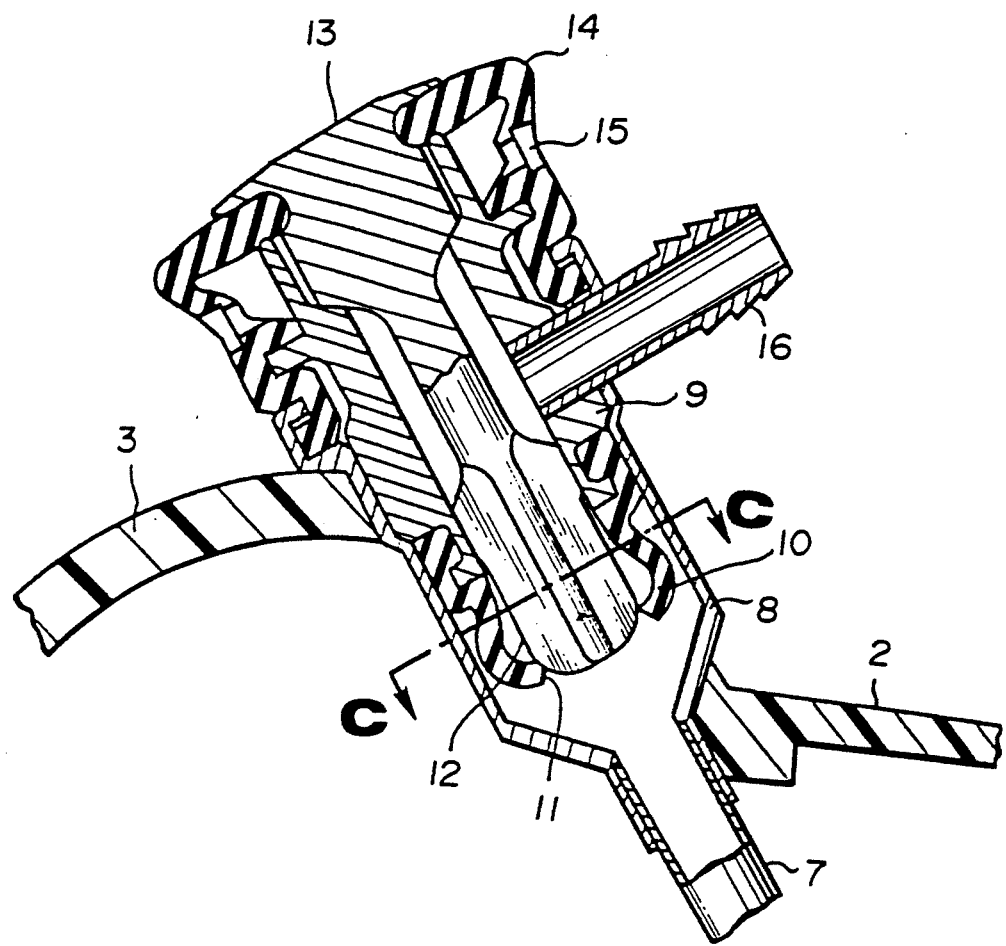
Figure 7:
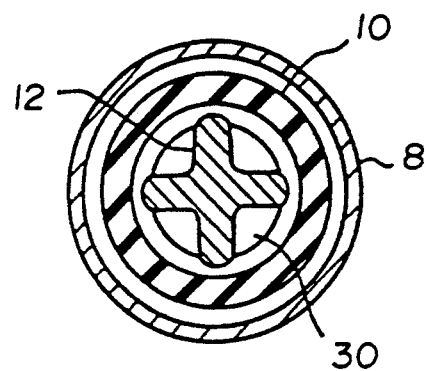

In such formation as is mentioned above, in case dirt and body fluids within a body cavity are to be sucked, the operating part 13 provided at the upper end of the operating member 12 is pushed with a finger and, as shown in FIG. 6, the lower end part of the operating member 12 is pushed into the slit 11 of the valve body 10. Then, as shown in FIG. 7, a clearance 30 will be produced between the operating member 12 and valve body 10, the slit 11 will open and, therefore, the sucking channel 7 and outer cylinder 8 will communicate with the inner cylinder 9 interior and mouthpiece part 16 so that the dirt and body fluids within the body cavity may be sucked out of the body cavity.

Thus, in the above-mentioned embodiment, the valve body 10 made of an elastic material is provided in the lower end part of the inner cylinder 9 removably fitting the outer cylinder 8, the bar-like operating member 12 is provided so as to be free to advance and retreat within the inner cylinder 9 and is pushed into the slit 11 of the valve body 10 so as to open the slit. Therefore, no valve seat is required to be provided in the outer cylinder 8. Therefore, the inner surface of the outer cylinder 8 can be made in a simple form easy to wash and the contagion by bad washing can be prevented.

In the above-mentioned embodiment, as the inner cylinder 9 is removably provided in the outer cylinder 8, the inner cylinder 9, valve body 10 and operating member 12 can be pulled at once out of the outer cylinder 8 and can be easily disassembled and washed.

Further, in the above-mentioned embodiment, as the leaking hole 15 is formed in the cover 14, even when the slit 11 of the valve body 10 is closed, the pressure within the inner cylinder 9 will not become negative, the slit will not be opened by the negative pressure and the dirt and body fluids within the body cavity will not enter the inner cylinder 9.

The cross-section of the operating member 12 need not be limited to be cruciform but may be of any other different form. FIG. 8 shows three modifications different in the form of the cross-section of the operating member 12 in FIG. 8.

Figure 8A:
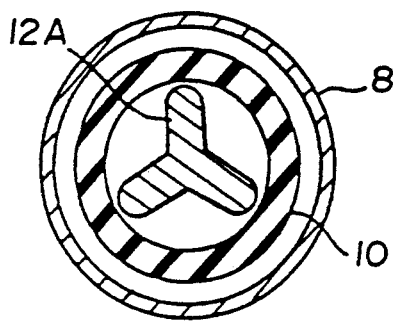
FIG. 8(a) shows a sectioned view of a first modification of the cross-sectioned shape of an operating member.

FIG. 8(a) shows the first modification in which the cross-sectioned shape of the operating member 12A is substantially Y-like. The same as in the cruciform cross-sectioned shape, when the lower end part of the operating member 12A is pushed in to open the slit 11, a clearance will be produced between the operating member 12 and valve body 10 and the dirt and the like within the body cavity will be able to be sucked by the sucking channel 7.

Figure 8B:
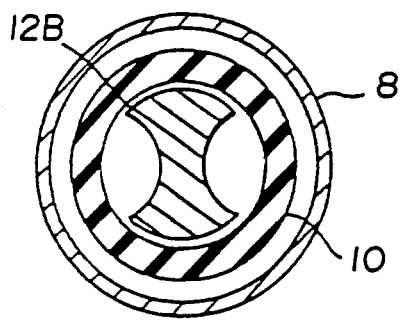
FIG. 8(b) shows a sectioned view of a second modification of the cross-sectioned shape of an operating member.

FIG. 8(b) shows the second modification in which the operating member 12B has two grooves formed in the axial direction on the periphery of a column and, in its cross-section, two clearances are formed opposed to one other. The operation of the second modification is the same as of the first modification.

Figure 8C:
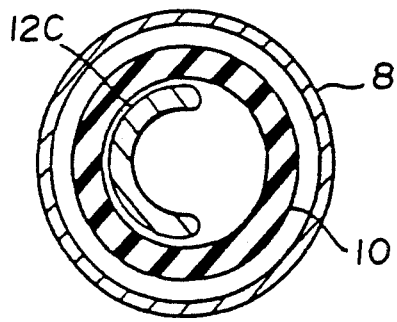
FIG. 8(c) shows a sectioned view of a third modification of the cross-sectioned shape of an operating member.

FIG. 8(c) shows the third modification in which the operating member 12C is of a substantially C-like cross-section In this modification, when the operating member 12C is pushed in, one clearance will be formed.

Figure 9:
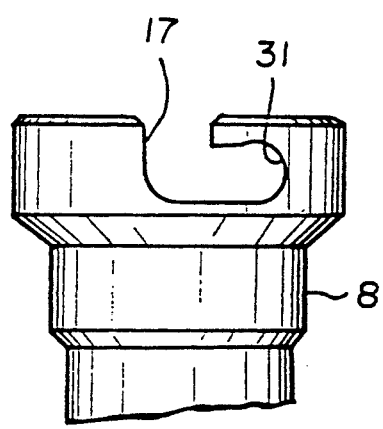

In the above-mentioned embodiment, the mouthpiece part 16 is engaged with the incised part 17 of the outer cylinder 8 but, as shown in FIG. 9, an engaging part 31 may be provided on the side of the incised part 17 and the mouthpiece part 16 may be engaged with this engaging part 31. In such formation, the inner cylinder 9 can be prevented from being removed from the outer cylinder 8 by mistake.

The second embodiment of the present invention shall be explained in the following with reference to FIGS. 10 to 14.

The second embodiment is an example in which the inner cylinder 9, valve body 10 and cover 14 are integrally formed.

Figure 10:
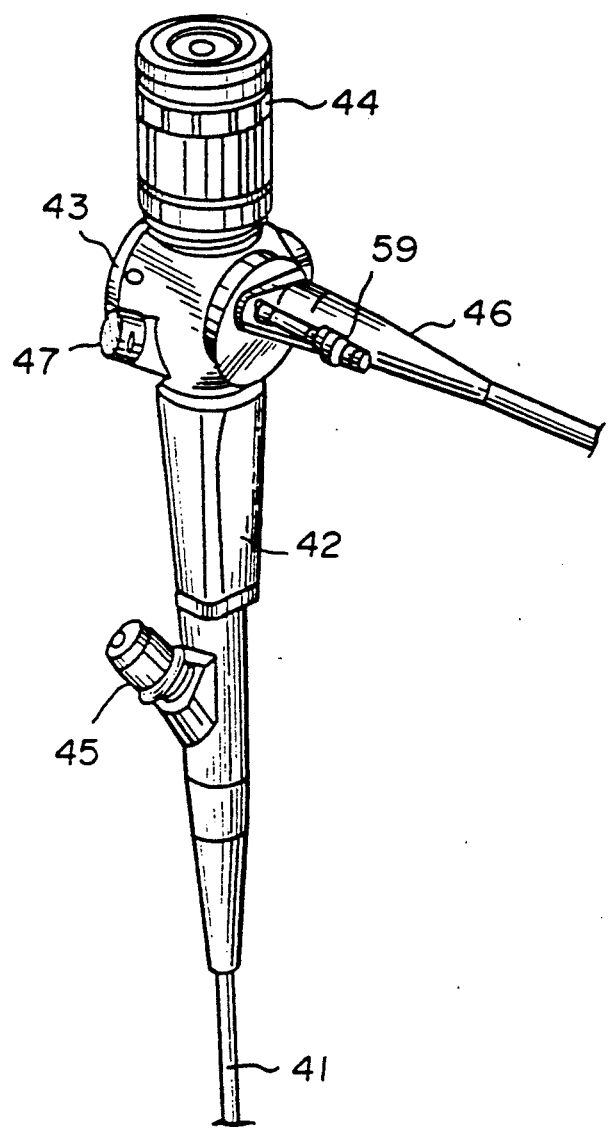
FIGS. 10 to 14 relate to the second embodiment of the present invention.

FIG. 10 is a view showing a schematic formation of an endoscope provided the same as in the first embodiment with a gripping part 42 at the rear end of an insertable part 41 to be inserted into a body cavity and is further provided with an operating part 43 and eyepiece part 44 at the rear end of the gripping part 42.

A treating instrument inserting part 45 for inserting such treating instrument as a forceps into a treating instrument channel formed within the insertable part 41 is provided at the rear end of the above-mentioned insertable part 41. The operating part 43 has a universal cord 46 connected on the side and is provided with a suction operating apparatus 47. A mouthpiece part 59 of the suction operating apparatus 47 is inserted through the operating part 43 and is extended out substantially in parallel with a universal cord 46. The universal cord 46 is provided at the tip with a connector connected to a light source not illustrated.

Figure 11:
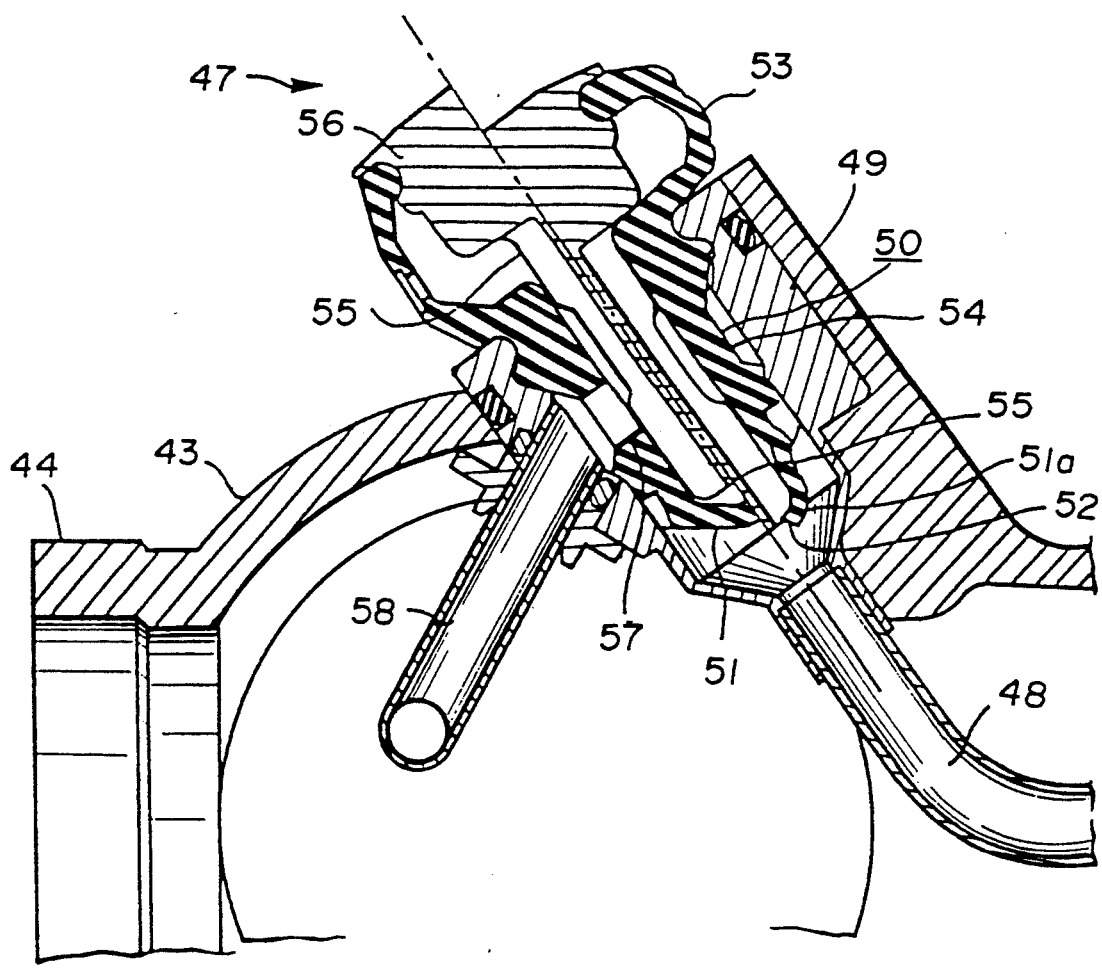

This suction operating apparatus 47 is formed as shown in FIG. 11. An outer cylinder 49 of the suction operating apparatus 47 is connected to a sucking channel 48 communicating with the treating instrument channel. A suction operating valve 50 made of an elastic material such as rubber is removably fitted in this outer cylinder 49. A valve body part 51 is integrally provided at the lower end of the suction operating valve 50. This valve body part 51 has a closing part 51a closing the opening of the suction operating valve 50 and a slit 52 formed in the center of the closing part 51a.

Also, the suction operating valve 50 is provided integrally at the upper end with a spring part 53 for elastically returning a later described operating member 55 to the fixed position An inner cylinder part 54 is formed between the spring part 53 and valve body part 51.

An operating member 55 is provided to be free to advance and retreat within the inner cylinder part 54 and is provided at the upper end with an operating part 56 for pushing the lower end part of the operating member 55 into the slit 52 of the valve part 51. As in the first embodiment, the operating member 55 is cruciform in the cross-section. In FIG. 11, the left side of the center line shows a non-sucking state in which the operating member 55 is not pushed in and the right side shows a suction operating state in which the operating member 55 is pushed in.

The suction operating valve 50 has a sucking hole 57 formed on the side of the inner cylinder part 54. This sucking hole 57 communicates with a mouthpiece part 59 (see FIG. 10) through a communicating tube 58 so that the dirt and body fluids within the body cavity may be sucked through the treating instrument channel by the sucking force of a sucking pump connected to the mouthpiece part 59.

Figure 12:
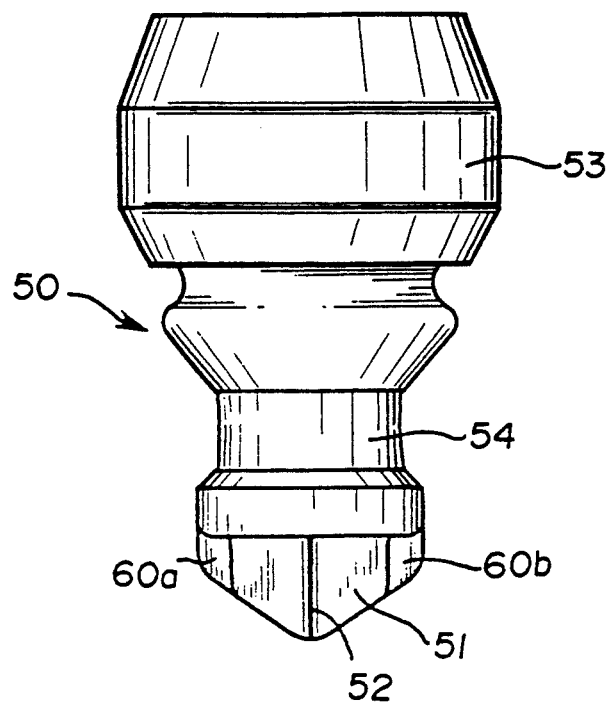
Figure 13:
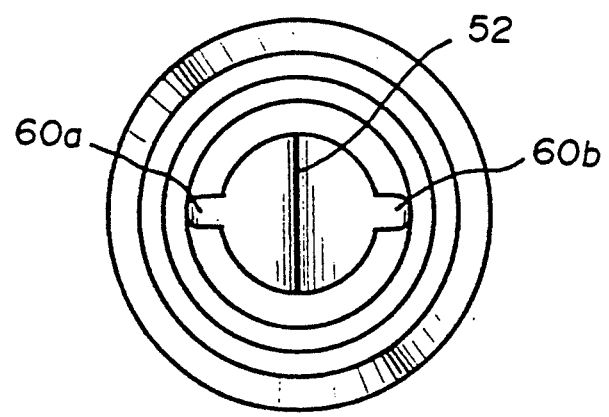
Figure 14:
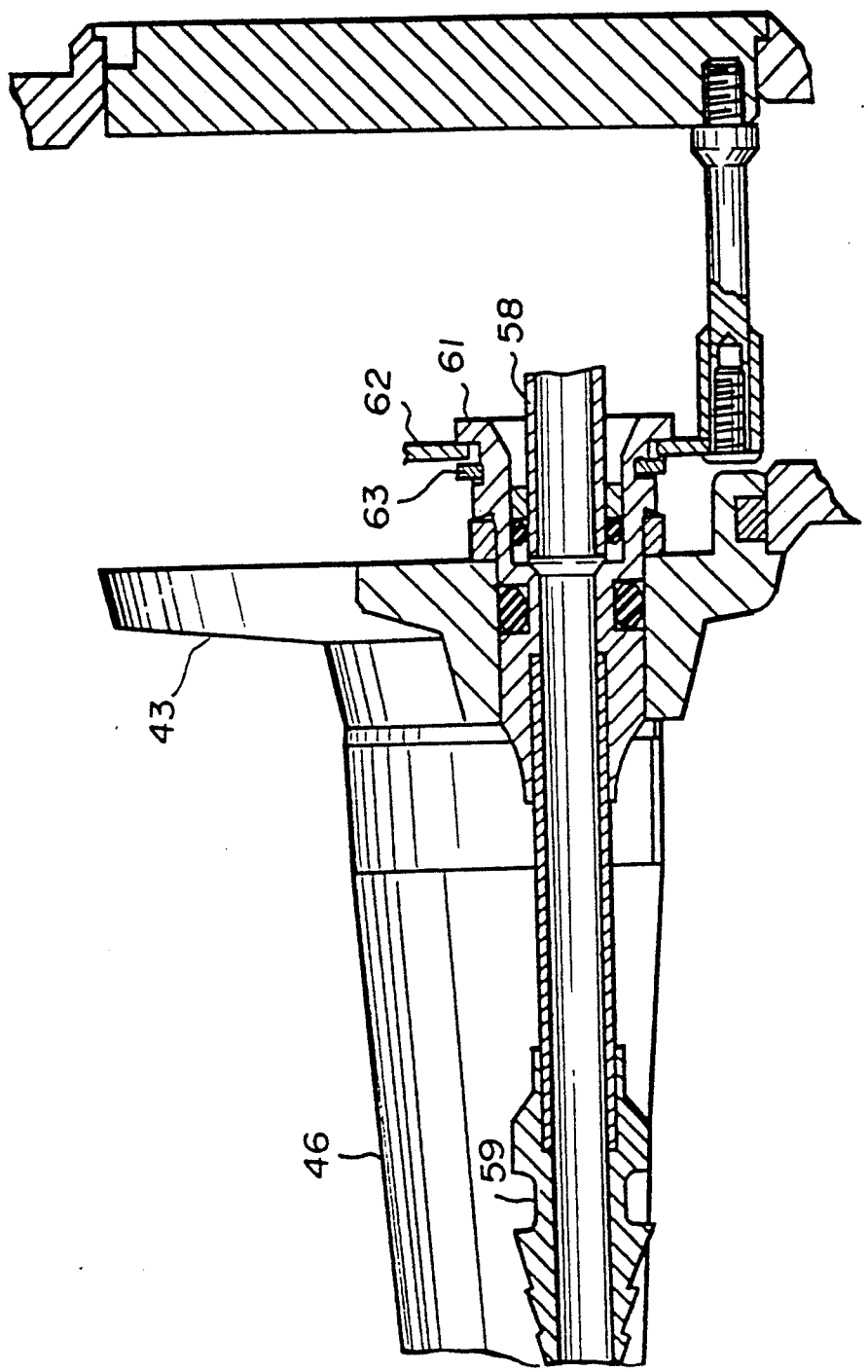

As shown in FIGS. 12 and 13, the suction operating valve 50 is provided with ribs 60a and 60b on both sides of the slit 52 on the outer wall of the valve body part 51 so that, by these ribs 60a and 60b, the slit 52 will be completely closed when the operating member 55 is standing by, that is, is not operating. As shown in FIG. 14, the mouthpiece part 59 is fixed to the operating part 43 through a fitting ring body 61 and supporting plate 62 and the fitting ring body 61 is provided with a crescent ring 63 for fixing the supporting plate 62.

As mentioned above, in the case of sucking dirt and body fluids within the body cavity, the same as in the first embodiment, the operating part 56 provided at the upper end of the operating member 55 is pushed with a finger to push the lower end part of the operating member 55 into the slit 52 of the valve body part 51. Then, as shown on the right side in FIG. 11, the slit 52 will open and therefore the dirt and body fluids within the body cavity will be able to be sucked out of the body cavity through the treating instrument channel. Therefore, even in this embodiment, the same as in the first embodiment, the inner surface of the outer cylinder 49 can be made in a simple form easy to wash, and contagion by bad washing can be prevented.

In the above-mentioned embodiment, as the valve body 51 is provided with the ribs 60a and 60b on both sides of the slit 52 in the outer wall part, the slit 52 will be able to be closed and to be prevented from sucking by mistake when the operating member 55 is standing by, that is, is not operated.

FIGS. 15 and 16 show the third embodiment of the present invention.

Figure 15A:
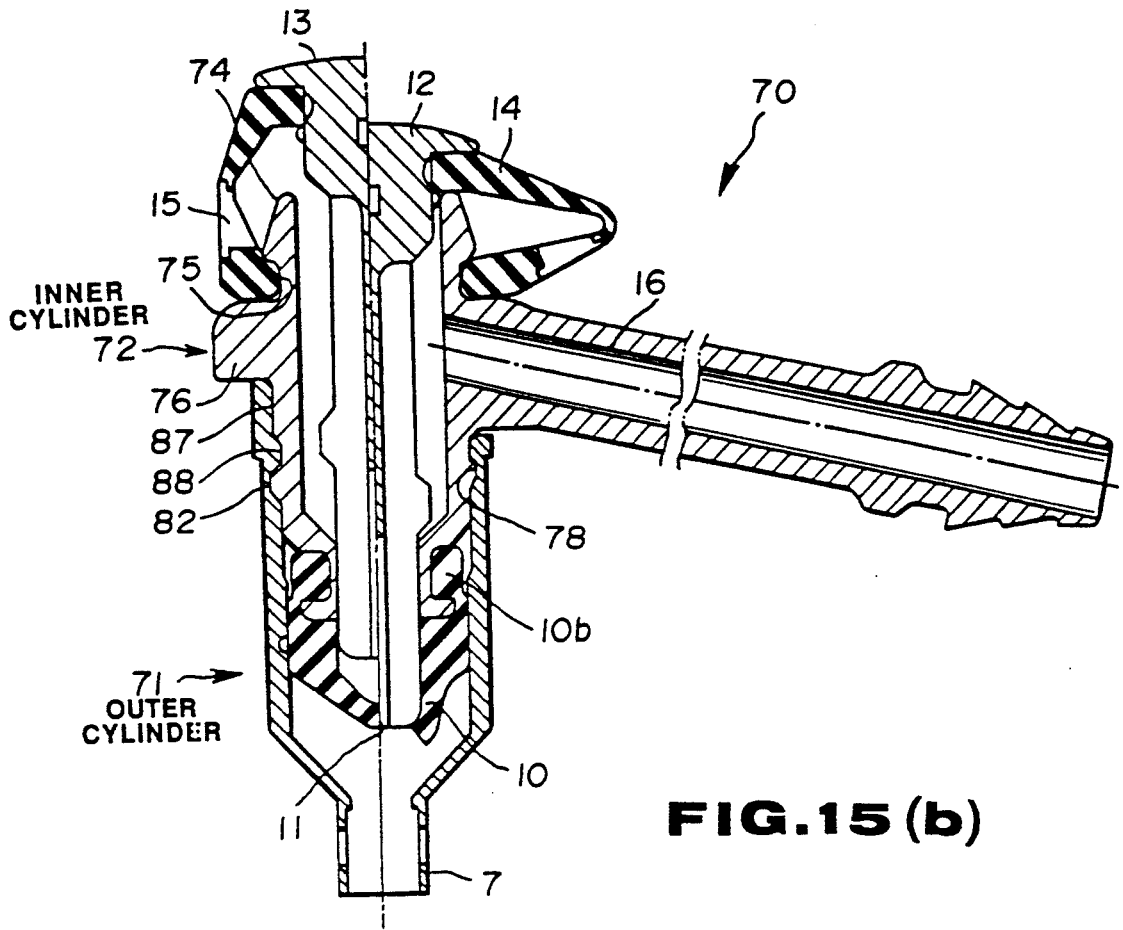
Figure 15B:
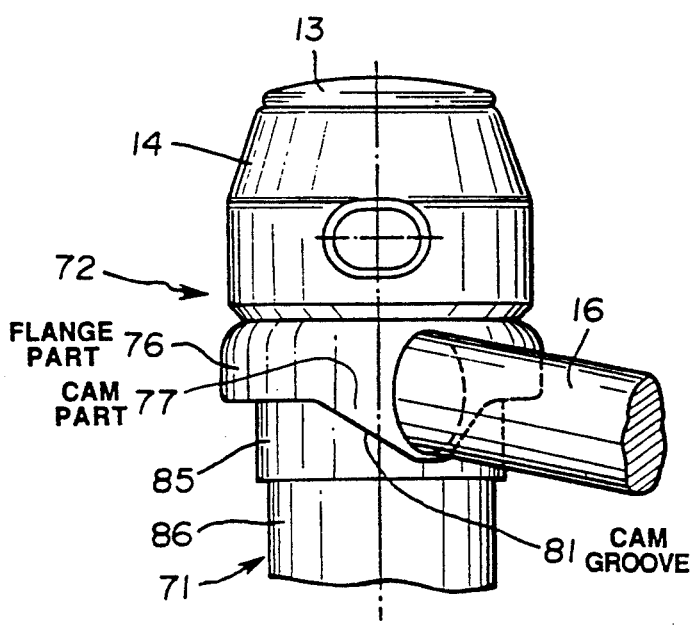
FIG. 15(b) is an elevation of the suction operating apparatus.

The third embodiment is an example in which the outer cylinder 8 and inner cylinder 9 in the first embodiment are changed in contour so as to be easy to fit and remove. In FIG. 15(a), the left side of the center line represents the manner before the operating part of the suction operating apparatus is pushed and the right side represents the manner after it is pressed. FIG. 15(b) shows an elevation of the suction operating apparatus. The same components as in the first embodiment shall bear the same reference numerals and shall not be explained here.

Figure 16A:
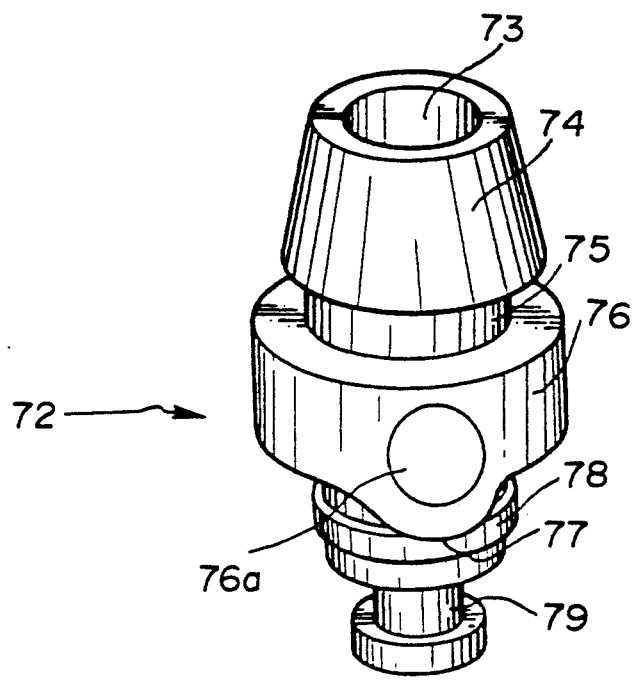
FIG. 16(a) is a perspective view of an inner cylinder with a mouthpiece part cut off.
Figure 16B:
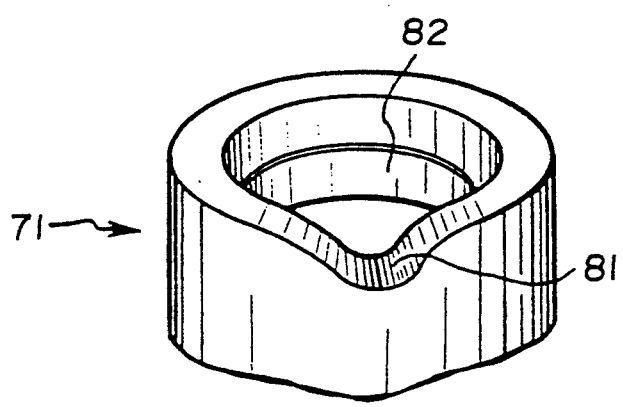
FIG. 16(b) is a perspective view of a large diameter part in the upper part of an outer cylinder.

A suction operating apparatus 70 comprises an outer cylinder 71 connected to the sucking channel 7 and an inner cylinder 72 removably fitted to this outer cylinder 71. FIG. 16(a) shows the inner cylinder 72 incised in the mouthpiece part. FIG. 16(b) shows a large diameter part in the upper part of the outer cylinder 71.

The above-mentioned inner cylinder 72 is made, for example, of a plastic member and is provided with a through hole 73 through which the operating member 12 is to be inserted to slide in the axial direction. A port part 74 formed to be tapered on the outer periphery is provided above in the axial direction and is provided annularly below with a groove part 75. Below the above-mentioned groove part 75 is provided a flange part 76 forming an end surface cam. The mouthpiece part 16 is formed to extend out of the side 76a of this flange part 76. In this embodiment, the mouthpiece part 16 is formed integrally with the inner cylinder 72. A cam part 77 forming a substantially U-like projection is formed on the end surface of the flange part 76 below the above-mentioned mouthpiece part 16. Further, a projection 78 as an engaged part having an inclined surface on the vertical surface is peripherally provided on the outer periphery below the cam part 77 of the above-mentioned inner cylinder 72 and a groove part 79 is provided on the outer periphery near the lower end of this inner cylinder 72.

The outer cylinder 71 is provided at its upper end with a cam groove 81 so as to correspond to the cam part 77 provided on the above-mentioned inner cylinder 72 and is provided on the inner peripheral surface with an engaging groove part 82 as an engaging part in the position corresponding to the projection 78 of the above-mentioned inner cylinder 72.

The projection 78 need not always be formed peripherally, two or three projections may be formed on the periphery and an engaged part engaged with the engaging groove part 82 of the outer cylinder 71 may be formed.

Returning to FIG. 15, the above-mentioned outer cylinder 71 comprises a large diameter part 85 having a cam groove 81 and a small diameter part 26 below it. The diameter of the inner periphery of an opening part 87 at the upper end of the cylinder is made larger than the outside diameter of the projection 78 provided on the inner cylinder 72. Further, a small diameter inner peripheral part 88 formed to be of a diameter rather smaller than the outside diameter of the above-mentioned projection 78 and an engaging groove part 82 engaged with the above-mentioned projection 78 are formed through an inclined surface.

A ring-like fitting part 10b of the valve body 10 made of an elastic member such as rubber is engaged with the groove part 79 at the lower end of the above-mentioned inner cylinder 72. Also, the cylindrical cover 14 made of an elastic member such as silicone rubber is engaged at one end with the groove part 75 at the upper end of the above-mentioned inner cylinder 72 and at the other end with a step part formed at the upper end of the above-mentioned operating member 12.

As in the first embodiment, the above-mentioned operating member 12 is formed to be cruciform in the cross-section and is provided at the upper end with an operating part 13 so as to be energized by the above-mentioned cover 14 to hold the position before being energized and compressed by the above-mentioned cover 14. When the operating part 13 is pressed, the above-mentioned operating member 12 will slide and the lower end part will be pushed into the slit 11 provided in the valve body 10 to open the valve body 10. This pressed operating member 12 will be returned to the original position by the energizing force of the cover 14.

The operation in the case of the sucking operation is the same as in the first embodiment. When the operating part 13 is pressed by a finger, as in the right side view in FIG. 15(a), the lower end part of the operating member 12 will be pushed into the slit 11, a clearance will be produced between the operating member 12 and slit 11. Therefore the dirt and body fluids within the body cavity will be drained out of the body cavity through a sucking pipe or sucking tube not illustrated connected to the mouthpiece part 16.

On the other hand, in case the suction operating apparatus 70 is to be disassembled and washed, when the inner cylinder 72 is rotated with respect to the outer cylinder 71 by holding the mouthpiece part 16 of the inner cylinder 72, by the end surface cam formed of the substantially U-like cam part 77 provided on the inner cylinder 72 and the cam groove 81 provided on the outer cylinder 71, the inner cylinder 72 will begin to gradually rise along the cam groove 81 and, at the same time, the projection 78 of the inner cylinder 72 engaged with the engaging groove part 82 of the outer cylinder 71 will begin to be pulled out. When this inner cylinder 72 is further rotated, the projection 78 of the inner cylinder 72 will be disengaged from the engaging groove part 82 of the outer cylinder 71 and the inner cylinder 72 will be pulled out of the outer cylinder 71. Thus, the mouthpiece part 16 of the inner cylinder 72 can be utilized as a lever, and the inner cylinder 72 can be easily pulled out of the outer cylinder 71 with a small force.

In the case of fitting the inner cylinder 72 after disassembling and washing it, when the inner cylinder 72 is pushed into the outer cylinder 71 so that the cam part 77 of the inner cylinder 72 corresponds to the cam groove 81 of the outer cylinder 71, the projection 78 and its periphery will be elastically deformed and will be engaged and fitted in a clicking sense with the engaging groove part 82 over the small diameter inner peripheral part 88 of the outer cylinder 71.

Thus, according to this embodiment, as the inner cylinder 72 can be easily removed from the outer cylinder 71 provided in the operating part 3, the interior of the inner cylinder 72 and outer cylinder 71 can be easily washed. The engaging groove part 82 of the outer cylinder 71 and the projection 78 of the inner cylinder 72 are not complicated in the contour and therefore can be worked comparatively easily.

The position of the cam part 77 provided on the inner cylinder 72 need not always be just below the mouthpiece part 16. However, if the cam part 77 is provided near the mouthpiece part 16 to be held in the case of removing the inner cylinder 72, operability will improve.

FIG. 17 shows the fourth embodiment of the present invention.

Figure 17A:
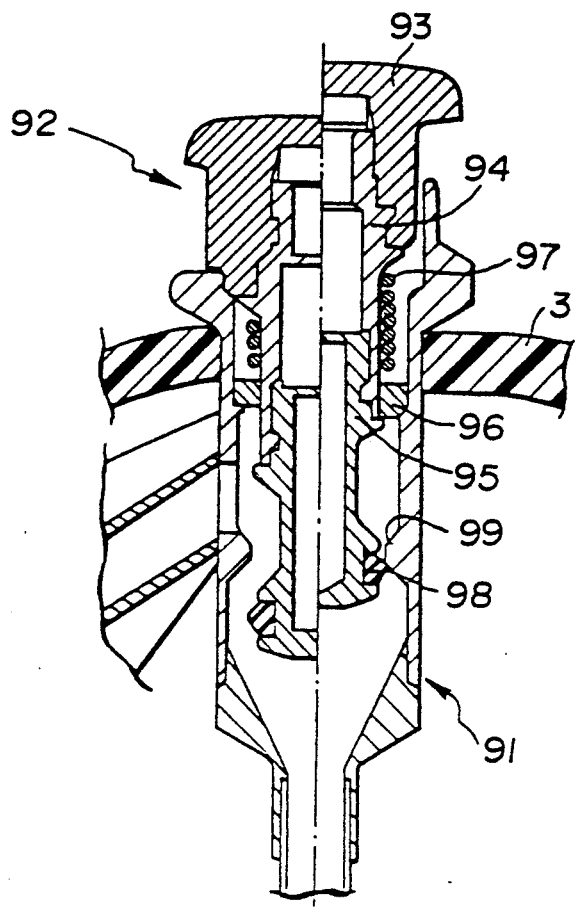
FIG. 17(a) shows a sectioned view of a suction operating apparatus relating to the fourth embodiment of the present invention.
Figure 17B:
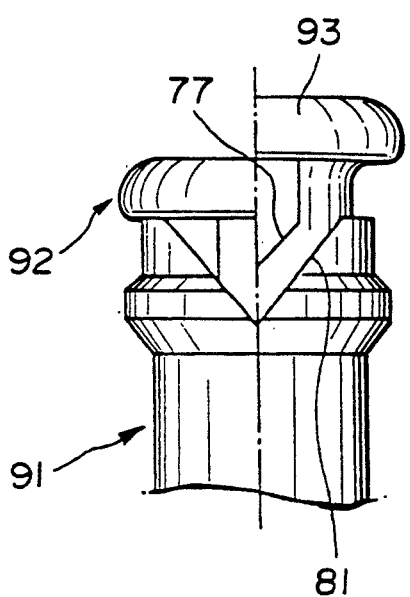
FIG. 17(b) shows an elevation view of a suction operating apparatus relating to the fourth embodiment of the present invention.

The fourth embodiment is a modification of the third embodiment. The left side of the center line in FIG. 17(a) shows a cross-section at the time of sucking and the right side shows a cross-section at the time of non-sucking. FIG. 17(b) shows an elevation of (a).

The suction operating apparatus of this embodiment is provided with an outer cylinder 91 and operating member 92. The above-mentioned outer cylinder 91 is fitted and bonded in the operating part 3 of the endoscope. The above-mentioned operating member 92 comprises an operating part 93 formed at the top and a first inner tube 94 and second inner tube 95 connected to this operating part 93. A coil spring 97 is annularly fitted on the outer periphery of the first inner tube 94 and contacts at one end with a spring receiving member 96 and contacts at the other end with a projection provided on the outer periphery of the fist inner tube 94. An annular elastic member 98 (engaged part) is fitted in a recess at the lower end of the second inner tube 95. A projection 99 (engaging part) formed to be smaller than the outside diameter of the elastic member 98 is formed on the inner peripheral surface of the outer cylinder 91. As in the third embodiment, the cam part 77 is provided on the above-mentioned operating part 93 and a cam groove 81 corresponding to the cam part 77 is provided at the upper end of the outer cylinder 91.

As in the third embodiment, by the projection 99 on the inner peripheral surface of the outer cylinder 91 and the elastic member 98 of the operating member 92, in a clicking sense, the operating member 92 can be fitted and, by rotating the operating member 92 with the cam groove 81 of the outer cylinder 91 and the cam part of the operating member 92, the operating member 92 can be simply removed from the outer cylinder 91.

FIGS. 18 to 23 show the fifth embodiment of the present invention.

The fifth embodiment is provided with a leaking amount varying mechanism whereby the size of the leaking path communicating with the outside is constructed such that, when not sucking, a sufficient leaking flow volume will be secured and, when sucking, the sucked substances will be prevented from spreading out.

In the conventional suction operating apparatus, the suction is made by opening with the operating member the valve body provided between the sucking port and sucking channel and closing with the elastic member the leaking clearance making the sucking port communicate with the atmosphere. Such a conventional apparatus suffers from defects that, when the valve body is opened, the leaking clearance will remain open to the outside and therefore the dirt and body fluids sucked through the sucking channel will spread out of the leaking clearance with the energy as it is and will be deposited on the hands and fingers of the operator. To counteract this it is desirable to bend the path from the sucking channel to the leaking clearance and prevent the sucked substances from spreading out. However, this prior art apparatus suffers from defects in that the pipeline formation will be complicated and the washability of the devices will reduce.

Therefore, in this embodiment, it is intended to solve these defects with the above-mentioned leaking amount varying mechanism. The same components as in the first embodiment shall bear the same reference numerals and shall not be explained here.

Figure 18:
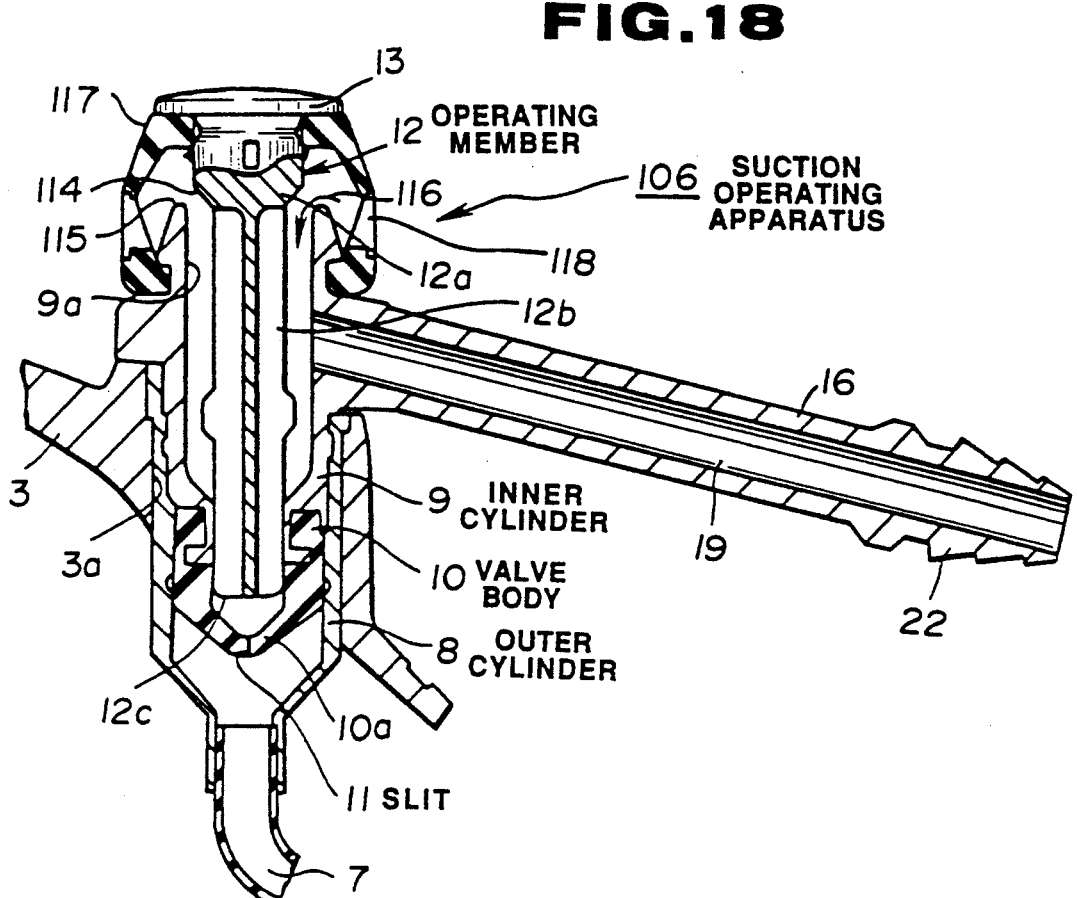
FIGS. 18 to 23 relate to the fifth embodiment of the present invention.

A suction operating apparatus 106 of this fifth embodiment will be of such structure as shown in FIG. 18 when no suction is operated. The same as in the first embodiment, in the suction operating apparatus 106, the outer cylinder 8 is fitted in the fitting hole 3a in the operating part 3 of the endoscope and the inner cylinder 9 is removably fitted in the outer cylinder 8. The inner cylinder 9 is provided at the lower end with the valve body 10 and within it with the bar-like operating member 13 so as to be free to advance and retreat. A substantially columnar leaking flow path adjusting member 12a is formed on the upper side of the operating member 2. The lower part 12b on the lower side of the leaking flow path adjusting member 12a is cruciform in the cross-section as in the first embodiment.

The above-mentioned lowered part 12b and operating part 13 are connected with each other through the leaking flow path adjusting member 12a of the columnar cross-section. The outside diameter of this adjusting member 12a is made smaller than the inside diameter of the upper inner surface 9a of the inner cylinder 9 so that, even when the adjusting member 12a is present inside this upper inner surface 9a, a small leaking flow path may be formed. The lower end part 114 of the adjusting member 12a is provided in the position approaching the upper end part 115 of the inner cylinder 9 when the lower end part 12c of the operating member 12 contacts the closing film 10a.

Figure 19:
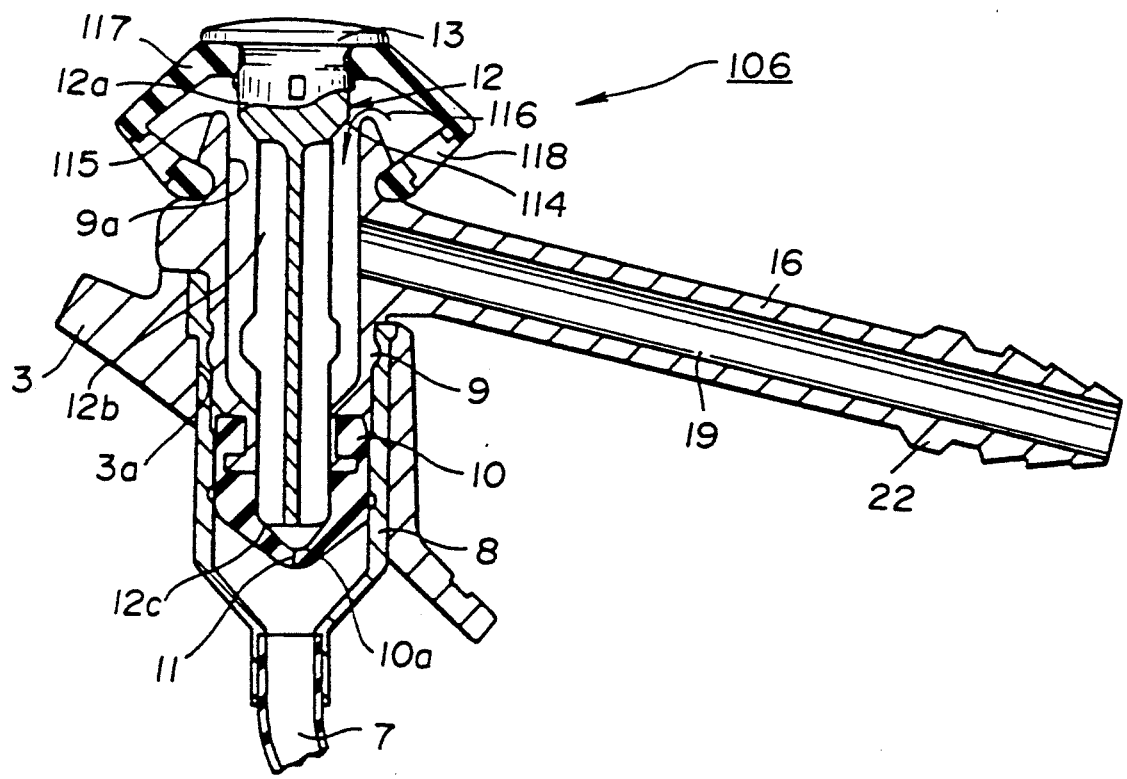

A leaking flow path 116 is formed of the upper inner surface 9a of the inner cylinder 9, the lower part of the operating member 12 and both outer surfaces of the leaking flow path adjusting member 12a. The cross-sectional area of this leaking flow path 116 is set to be substantially below ½ that shown in FIG. 18 from the state when the lower end part 114 of the adjusting member 12a is adjacent to the upper end part 115 of the inner cylinder 9 as shown in FIG. 19 until just before the state in FIG. 20.

A cover 117 is engaged at the lower end with a recess provided near the upper end part 115 of the inner cylinder 9 and is fitted at the upper end to contact a column adjacent to the operating part 13 of the operating member 12. This cover 117 is formed of an elastic material such as rubber to be shaped like a cylinder having a diameter of the central part larger than of both end parts so as to have an elasticity in the axial direction when the central part is bent. The operating member 12 is energized to be able to return the inner cylinder 9 to the fixed position, that is, the state shown in FIG. 18 (after the operating member 12 is moved downward to the state shown in FIG. 20) by the elastic force of this cover.

In this cover 117, a leaking hole 118 for sucking the atmosphere is formed from the central part toward the lower end of the cover 117. As shown in FIG. 18, when the leaking flow path 116 is secured, that is, in case the sucking operation (of pushing in the operating part 13) is not made, the above-mentioned leaking hole 118 will communicate with the sucking path 19 of the mouthpiece 16 through the leaking flow path 116.

The base end part of the mouthpiece part 16 forming the sucking path 19 is integrally formed on the side of the inner cylinder 9. A sucking pump, not illustrated, is to be connected to the connecting part 22 at the tip of this mouthpiece part 16 through a sucking tube so that (when a sucking operation to close the leaking flow path is made) the dirt and body fluids within the body cavity may be sucked by the sucking force of the sucking pump (the state in FIG. 20).

Figure 20:
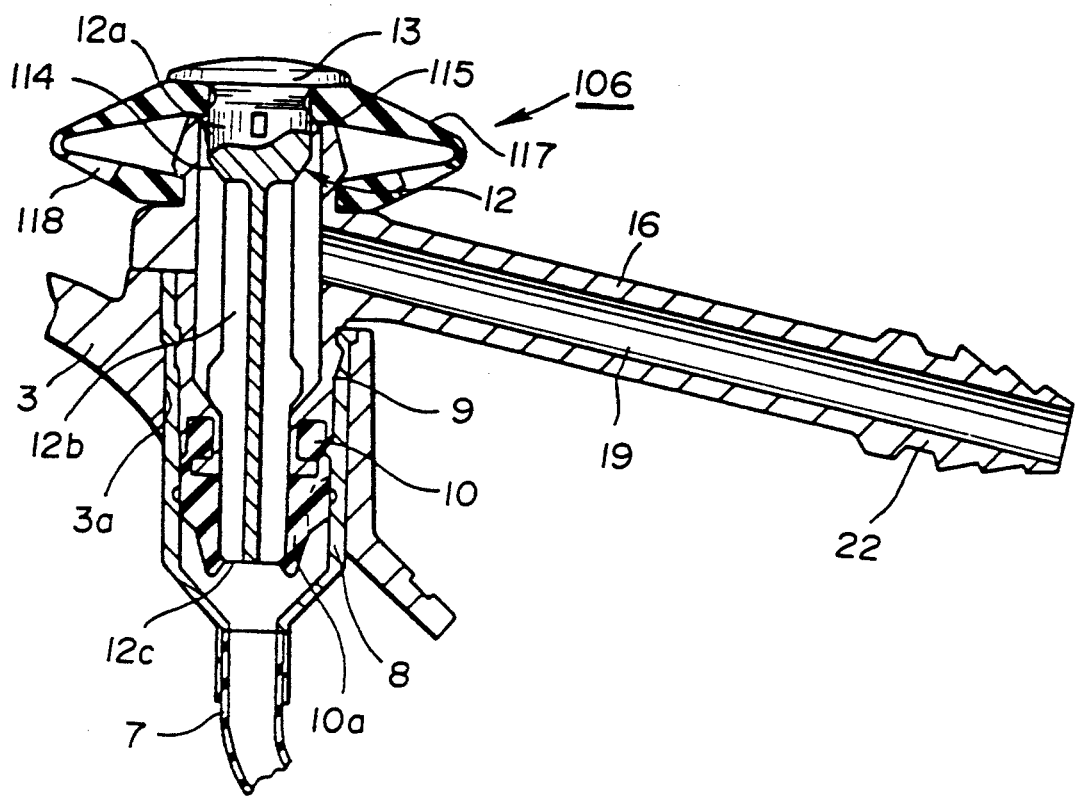

As shown in FIG. 18, in case no sucking operation is made, the sufficient leaking flow path 116 will be secured, as shown in FIG. 19, while the sucking operation is made, just before the slit of the valve body 10 is opened, the cross-sectional area of the leaking flow path 116 will be kept to be smaller than, for example, ½ in the part of the enlarged diameter of the leaking flow path adjusting member 12a (the part above the lower end part 114). Then, as shown in FIG. 20, when the slit 11 of the valve body 10 is opened, the leaking flow path 116 will be closed.

The leaking amount varying mechanism is formed whereby at least before such end period of the sucking operation as the initial period of the stroke of pushing in the operating member 12 in the case of the sucking operation, the cross-sectional area of the leaking flow path will be reduced to be at least smaller than when it is not pushed in and, in the final pushing position of the predetermined stroke movement, the leaking flow path 116 will be completely closed. By this leaking amount varying mechanism, when the valve body 10 is opened, the cross-sectional area of the leaking flow path 116 will be made smaller than at least when it is closed.

Therefore, when not sucking, a sufficient leaking flow volume will be secured and, when sucking, the cross-sectional area of the leaking flow path 11 will be reduced so that the sucked substances sucked through the sucking channel 7 in the case of sucking will be able to be effectively prevented from spreading out to be deposited on the operator and the valve body 10 will be able to be positively opened and closed.

The operation of this embodiment shall be explained in the following.

In such formation as is mentioned above, when not sucking (the state in FIG. 18), by the sucking pressure given into the inner cylinder 9 through the mouthpiece 16, the atmosphere will be sucked through the leaking flow path 116 having a sufficient cross-sectional area from the leaking hole 118. Then, in the case of sucking the dirt and body fluids within the body cavity, when the operating part 13 is pushed to push in the operating member 12 downward against the elastic force of the cover 117, as shown in FIG. 19, the lower end part 12c of the operating member 12 will contact the closing film 10a and will tend to push open the slit 11 of the valve body 10, the lower end part 114 of the leaking flow path adjusting member 12a will approach the upper end part 115 of the inner cylinder 9 and the cross-sectional area of the leaking flow path 116 will quickly reduce.

Therefore, at this time, the pressure of the inner cylinder 9 will be the lowest. Further, when the operating part 13 is pushed in, as shown in FIG. 20, the lower end part 12c of the operating member 12 will push and expand the slit 11 of the valve body 10, the interior of the inner cylinder 9 will communicate with the sucking channel 7 and the dirt and body fluids will begin to be sucked and, when the upper end part 115 of the inner cylinder 9 contacts the cover 117, the leaking flow path 116 will be completely closed. When pushing the operating part 13 is stopped and the finger is released, by the elastic force of the cover 117, the operating member 12 will be moved in the direction reverse to the pushed movement, that is, upward and the non-sucking state shown in FIG. 18 will return.

Therefore, according to this fifth embodiment, substantially simultaneously with opening the valve body 10 and starting sucking the dirt, the leaking flow path 116 will be quickly narrowed and therefore the dirt can be effectively prevented from spreading out through the leaking flow path 116. Also, since the leaking hole 118 is provided downward in the cover 117, the leaking hole 118 will not be closed with the finger and, even if the sucked fluids spread out, they will be directed downward and will be able to be prevented from being deposited on the finger.

When not sucking, the leaking flow path 116 of a sufficient cross-sectional area will be secured, therefore the interior of the inner cylinder 9 will not be under an excessive negative pressure and the valve body 10 will be smoothly and positively opened and closed.

Also, as the leaking flow path 116 need not be in a complicated form, the washability of the device provided with this suction operating apparatus 106 will be high.

Further, as the negative pressure within the inner cylinder 9 can be elevated just before opening the valve body 10, the operation at the time of starting sucking will rise fast and a suction of good response will be able to be made.

Figure 21:
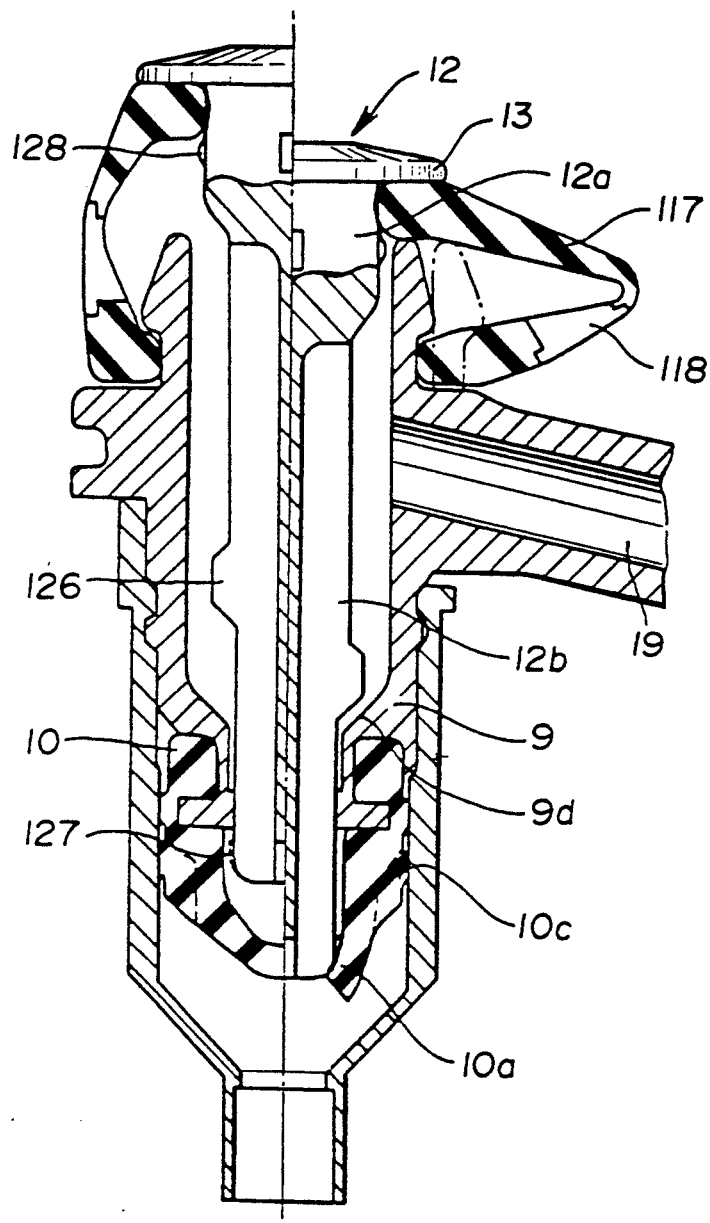

Also, in this embodiment, as shown in FIG. 21, a projection 10c is provided on the outer peripheral surface in contact with the inside wall of the outer cylinder 8 in the valve body 10. (In FIG. 21, the left half shows the non-sucking state and the right half shows the sucking state.) On the other hand, the inner peripheral surface of the outer cylinder 8 is treated to be smooth with chemical grinding or the like. By providing the above-mentioned projection 10c, the area of the contact surface with the outer cylinder 8 will be reduced, the friction with the cylinder will be reduced and the state of not operating the valve body 10 to suck after the sucking operation (that is, the state shown in FIG. 18) will be able to be positively returned.

Also, as the inside surface of the outer cylinder 8 is made smooth, the frictional force will be able to be made smaller and the slit 11 of the valve body 10 will be able to be more positively opened and closed. It is prevented that, in case this projection 10 is not provided, even after the sucking operation, by the frictional force, the slit 11 will remain open.

A projection 126 is provided on the lower part 12b of the operating member 12. On the other hand, an engaging part 9d made smaller in the diameter as tapered is engaged with this projection 126 on the lower end side of the inner cylinder 9 to form a regulating means regulating the operating member 12 to move downward from the position in which the projection 126 contacts the engaging part 9d.

As shown in the right half in FIG. 21, when the cover 117 is fitted, before the projection 126 contacts the engaging part 9d, the upper end part 115 of the inner cylinder 9 will contact the cover 117 and, therefore, the projection 126 will not happen to contact the engaging part 9d. However, because this apparatus 6 is easy to disassemble it may happen to be assembled without fitting the cover 117 after being washed or the like.

Figure 22:
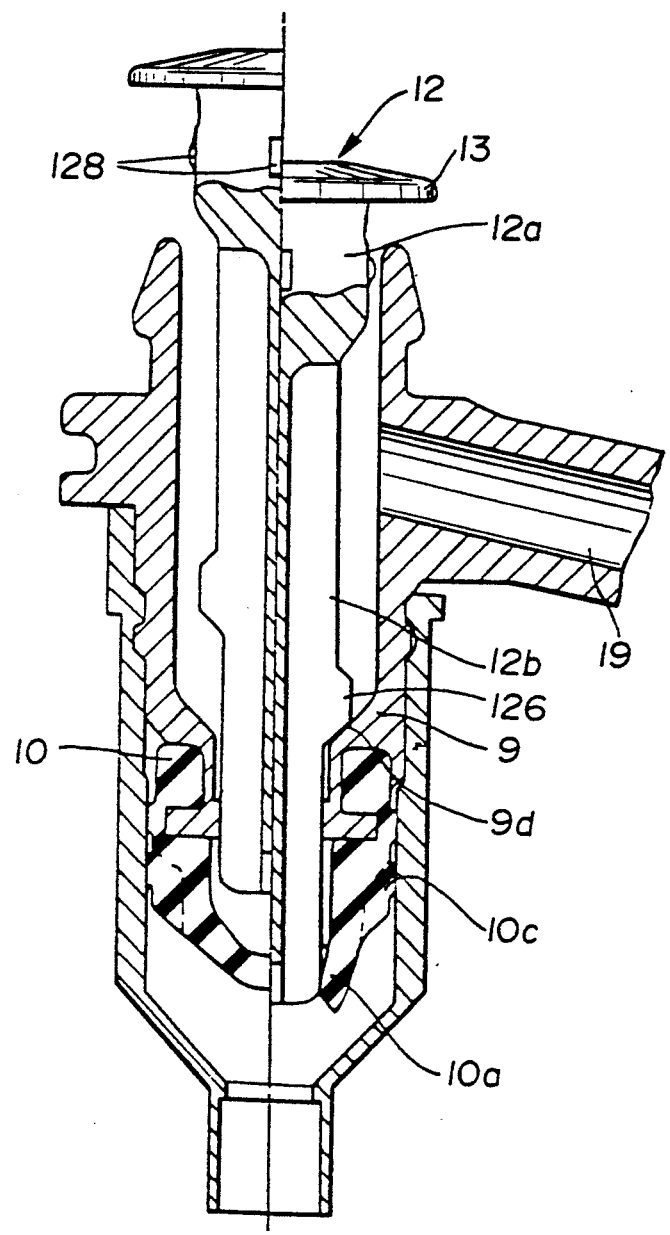

In such case, when the regulating means is not formed, once the operating part 13 is pushed in, the leaking flow path 116 will be kept closed causing a constant sucking state which is dangerous. On the other hand, if this regulating means is formed, as shown in FIG. 22, before the leaking flow path 116 is closed by this regulation means, the projection 126 will contact the engaging part 9d and the movement will be regulated. Therefore, the suction will be able to be set while leaking and will be able to be prevented from becoming dangerous.

As shown by the dotted line in FIG. 21, a projection 127 engaging with the lower end of the inner cylinder 9 may be provided on the lower end side of the operating member 12 so that, even if this operating member 12 is attempted to be pulled out, the projection 127 will catch on the lower end of the inner cylinder 9 and the structure will not be able to be disassembled.

Also, in this embodiment, as shown in FIG. 21, a projection 128 for preventing pulling out (the cover 117) is provided on the side of the columnar leaking flow path adjusting member 12a, a housing recess for housing the cover 117 is formed in the space between this projection 128 and operating part 13 and the top side (upper end part 115) of the inner cylinder 9 is formed adjacently to the side of this columnar leaking flow path adjusting member 12a.

As shown by the one-point chain line in FIG. 21, if the top side of the inner cylinder 9 is formed as separated from the side of the leaking flow path adjusting member 12a, in the case of housing the cover 117 in the housing recess at the time of assembling, the cover part in the opposite position will be pushed by the top part of this inner cylinder 9, the pushed position will be a position separate from the inner peripheral side end part of the cover 117, and the inner peripheral side end part of the cover 117 will not be able to pass over the projection 128 for preventing pulling out and the cover 117 will not be well-housed However, if it is provided adjacently to the side of the leaking flow path adjusting member 12a, the position near the inner peripheral side end part of the cover 117 will be pushed and therefore the inner peripheral side end part of the cover 117 will be able to be positively housed in the housing recess.

Figure 23:
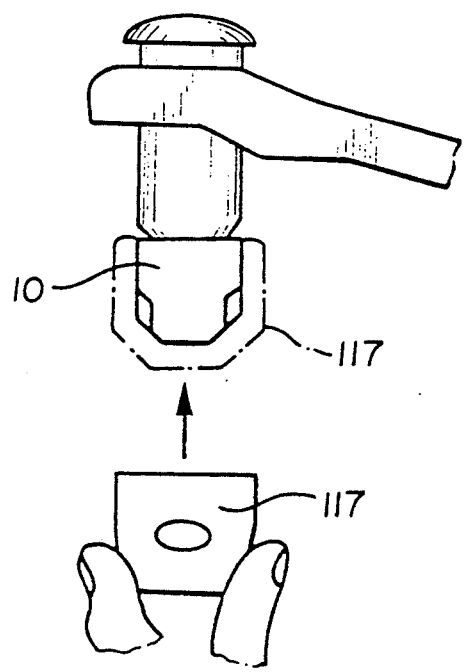

In the case of disassembling the suction operating apparatus 106, the valve body 10 which is formed of rubber and is small will be difficult to remove from the inner cylinder 9. In this embodiment, the diameter of one side opening of the cover 117 is made larger than the outside diameter of the valve body 10 so that the valve body 10 may be fitted in the opening of the cover 117 and therefore, as shown in FIG. 23, the cover 117 made of rubber is fitted in from the lower side of the valve body 10 so that the valve body 10 together with the cover 117 may be easily removed.

By the way, this embodiment is not limited to reducing the leaking amount in the initial period of the push-in stroke and the leaking amount may be reduced at least before the final position of the push-in stroke.

Figure 24:
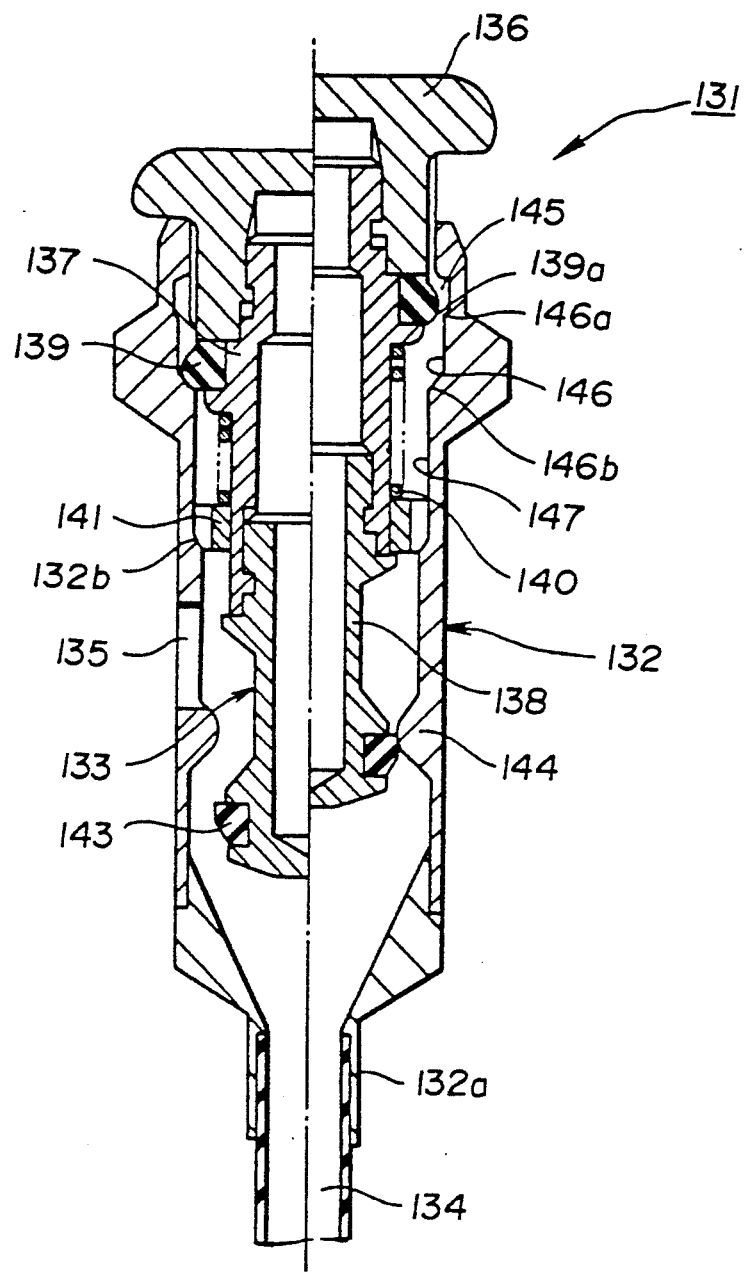
FIG. 24 is a sectioned view showing a suction operating apparatus relating to the sixth embodiment of the present invention.

FIG. 24 shows a suction operating apparatus 131 in the sixth embodiment of the present invention. In this FIG. 24, the cross-section on the left side of the center line shows the structure when sucking and the cross-section on the right side shows when not sucking.

The suction operating apparatus 131 comprises a cylindrical outer cylinder 132 and an operating member 133. The outer cylinder 132 is fitted and bonded in the body of the endoscope operating part 3. A mouthpiece part 132a at the lower end of the outer cylinder 132 is connected to a tube forming a sucking channel 134. A sucking hole 135 communicating with a sucking apparatus is formed on the side of this outer cylinder 132.

The above-mentioned operating member 133 comprises an operating part 136 formed at the top, a first inner tube 137 to which a cylinder part on the base end side of this operating part 136 is fitted and a second inner tube 138 to which this first inner tube is fitted at the other end.

A first elastic member 139 functioning as a leaking flow path adjusting member is annularly fitted to the first inner tube 137 in a recess adjacent to a projection and a coil spring 140 is annularly fitted adjacently to this projection. The coil spring 140 contacts at one end with this projection and at the other end with a spring receiving member 141 positioned on a tapered step part 132b of the outer cylinder 132 so that, by this coil spring 140, the projection formed on the first inner tube 137 may be energized upward and therefore the operating member 133 may be energized upward. A second elastic member 143 is annularly fitted in a recess formed near the lower end of the second inner tube 138. When no suction is operated, this second elastic member 143 will contact a projection 144 formed on the inside surface of the outer cylinder 132 and the sucking hole 135 formed on the side above this projection 144 will communicate with a leaking flow path 145. As shown on the left side in FIG. 24, when the suction is operated, the sucking hole 135 will separate from the projection 144 and will communicate with the channel 134.

This second elastic member 143 forms a valve body connecting or disconnecting the sucking hole 135 and sucking channel 134 with each other. Further, when the suction is operated, the leaking flow path 145 will be closed. A hole or groove for connecting the sucking hole 135 and leaking flow path 145 with each other when not sucking is formed in the spring receiving member 141.

On the other hand, the outside diameter of the first elastic member 139 functioning as a leaking flow path adjusting member is set to be slightly smaller than the inside diameter of the upper side inside surface 146 of the cylinder 132 so that, at the same time as the second elastic member 143 separates from the projection 144, the lower end part 139a will approach the upper step part 146a of the upper inside surface 146 to make the cross-sectional area of the leaking flow path small.

This upper inside surface 146 forms the cylinder inside surface connected to the lower inside surface 147 of an inside diameter smaller than of the above-mentioned upper inside surface 146 provided on the lower side through the lower step part 146 tapered in the form. Therefore, when the operating part 136 is pushed in and, as shown on the left side in FIG. 24, the first elastic member 139 contacts the lower step part 146, the leaking flow path 145 formed of the inside surfaces 147 and 146 of the outer cylinder 132, the operating member 133 and the vertical groove formed on the cylinder part of the operating part 136 will be completely interrupted.

The operation of this embodiment shall be explained in the following.

In the above-mentioned formation, when not sucking, the atmosphere will be sucked into the outer cylinder 132 and will be sucked into an outside sucking apparatus not illustrated. Then, in the case of sucking from the sucking channel, when the operating part 136 is pushed, the operating member 143 will be pulled off the projection 144 within the cylinder against the coil spring 140. Then, at the same time, the lower end part 139a of the first elastic member 139 forming the leaking flow path adjusting member will approach the upper step part 146a of the upper inside surface 146 so that the cross-sectional area of the leaking flow path 145 formed of the clearance between them will be quickly decreased.

When the operating part 136 is further pushed in, as shown in the left cross-section in FIG. 24, the elastic member 143 will sufficiently separate from the projection 144, the sucking tube path will be secured and the first elastic member 139 will collide with the lower step part 146 on the upper inside surface 146 to completely close the leaking flow path 145.

This embodiment has substantially the same effect as of the fifth embodiment.

In the above-described fifth and sixth embodiments is formed a leaking amount varying mechanism whereby, just before the valve is opened, the cross-sectional area of the leaking flow path will be made small to be substantially below $\frac{1}{2}$ of the cross-sectional area when fully open and, at the moment when the valve begins to open and the sucking channel and leaking flow path communicate with each other, the sucked substances will be substantially prevented from spreading out of the leaking hole through the leaking flow path.

When the leaking flow path is thus secured to any extent during the pushing-in stroke, even if the operator carelessly pushes the operating part, so long as the operating member is not pushed in completely to the final position, as the leaking flow path communicates with the sucking flow path, no strong suction will be made from the endoscope tip and thereby ensuring safety.

The function of the above-mentioned leaking amount varying mechanism may be changed in response to the sucking force by the sucking apparatus and the kind of the endoscope. For example, in case the sucking force by the sucking apparatus is large, the leaking amount before the valve opens may be made substantially zero or perfectly zero. Also, for example, in the fifth embodiment shown in FIG. 18, a ring or the like may be annually fitted to the leaking flow path adjusting member 12a part so that, by varying the outside diameter of this ring, a leaking amount varying mechanism adapted to the endoscope may be formed. In the sixth embodiment shown in FIG. 24, by replacing the first elastic member 139, the leaking amount can be varied.

In the above-described embodiments, examples of a suction operating apparatus used in an optical endoscope are shown but, the suction operating apparatus can be applied to an electronic endoscope apparatus.

In the present invention, it is apparent that working modes different in a wide range can be formed on the basis of the present invention without deviating from the spirit and scope of the invention. The present invention is not restricted by its specific working mode except that it is limited by the appended claims.

We claim:

1. An endoscope suction operating apparatus, comprising:
   an outer cylinder connected to a sucking channel of an endoscope and provided at its upper end with a cam groove;
   a sucking flow path which provides, via said cylinder, a communication between said sucking channel and a sucking hole connected to a sucking apparatus;
   an elastic valve body for making and breaking communication between said sucking flow path and said sucking channel;
   an inner cylinder having a cam part for cooperation with said cam groove of said outer cylinder and rotatably received in said outer cylinder, wherein said elastic valve body has a slit and is provided on at least the lower end of said inner cylinder; and
   a pushing operating member which is axially movable in said inner cylinder and elastically connected to said outer cylinder so as to open and close said slit of said elastic valve body.

2. An endoscope suction operating apparatus according to claim 1, wherein said outer cylinder has an engaging part provided on the inner peripheral surface thereof, and wherein said inner cylinder has an engaged part which, when said inner cylinder is pushed into said outer cylinder, engages with said engaging part of said outer cylinder as to limit the axial position of said inner cylinder.

3. An endoscope suction operating apparatus according to claim 1, wherein said inner cylinder has a mouthpiece part to be at end of said sucking flow path.

4. An endoscope suction operating apparatus according to claim 3, wherein said mouthpiece part is shaped to extend laterally from the outer periphery of said inner cylinder so that said inner cylinder can be rotated relative to said outer cylinder by being operated at said mouthpiece part.

5. An endoscope suction operating apparatus according to claim 4, wherein said mouthpiece part extends substantially in the same direction as a universal cord of the endoscope.

6. An endoscope suction operating apparatus according to claim 4, wherein said mouthpiece part is located at a position which is slightly offset from the universal cord of the endoscope from the position of the eyepiece portion of said endoscope.

7. An endoscope suction operating apparatus according to claim 1, wherein said cam groove of said outer cylinder is formed on the upper end of said outer cylinder, and said cam part of said inner cylinder is formed on the lower end surface of a flange part which is provided on said inner cylinder so as to project therefrom.

8. An endoscope suction operating apparatus according to claim 1, wherein said cam groove of said outer cylinder is formed on the upper end surface of said outer cylinder and said cam part of said inner cylinder is formed on the lower end of an operating part which is provided on the top of said inner cylinder.

9. An endoscope suction operating apparatus according to claim 8, wherein said cam groove and said cam part are substantially V-shaped.

10. An endoscope suction operating apparatus according to claim 8, wherein each of said cam groove and said cam part has an asymmetrical V-shaped with left and right wings inclined at different angles.

11. An endoscope suction operating apparatus, comprising:
    an outer cylinder connected to a sucking channel of an endoscope and provided at its upper end with a cam groove;
    a sucking flow path which provides, via said cylinder, a communication between said sucking channel and a sucking hole connected to a sucking apparatus;

an elastic valve body for making and breaking communication between said sucking flow path and said sucking channel;

an inner cylinder having a cam part for cooperation with said cam groove of said outer cylinder and rotatably received in said outer cylinder; and an operating part connected to the top portion of said inner cylinder for axially moving said inner cylinder within said outer cylinder, wherein said elastic valve body includes a ring-shaped elastic member which is provided on the outer peripheral surface of said inner cylinder at a lower portion of said inner cylinder, and said outer cylinder is provided with an engaging part projecting from the inner peripheral surface thereof, said ring-shaped elastic member being adapted to be moved into and out of contact with said engaging part when said operating part is actuated to cause axial movement of said inner cylinder so as to perform valve function.

* * * * *